United States Patent
Anwer (10) Patent No.: US 9,724,622 B2
(45) Date of Patent: Aug. 8, 2017

(54) PURIFICATION OF ORGANIC COMPOUNDS USING SURROGATE STATIONARY PHASES ON REVERSED PHASE COLUMNS

(71) Applicant: NEULAND HEALTH SCIENCES PRIVATE LIMITED, Hyderabad (IN)

(72) Inventor: Mohammed Khalid Anwer, Hyderabad (IN)

(73) Assignee: NEULAND HEALTH SCIENCES PRIVATE LIMITED, Hyderabad (IN)

( * ) Notice: Subject to any disclaimer, the term of this patent is extended or adjusted under 35 U.S.C. 154(b) by 0 days.

(21) Appl. No.: 14/763,831

(22) PCT Filed: Jul. 1, 2013

(86) PCT No.: PCT/IN2013/000403
§ 371 (c)(1),
(2) Date: Jul. 28, 2015

(87) PCT Pub. No.: WO2014/118797
PCT Pub. Date: Aug. 7, 2014

(65) Prior Publication Data
US 2015/0360146 A1 Dec. 17, 2015

(30) Foreign Application Priority Data

Jan. 29, 2013 (IN) .............................. 383/CHE/2013

(51) Int. Cl.
| | |
|---|---|
| C07K 1/20 | (2006.01) |
| C07K 7/06 | (2006.01) |
| B01D 15/36 | (2006.01) |
| B01D 15/42 | (2006.01) |
| B01D 15/32 | (2006.01) |
| B01D 15/20 | (2006.01) |
| G01N 30/88 | (2006.01) |

(52) U.S. Cl.
CPC .......... B01D 15/325 (2013.01); B01D 15/20 (2013.01); B01D 15/36 (2013.01); B01D 15/424 (2013.01); C07K 1/20 (2013.01); C07K 7/06 (2013.01); G01N 2030/884 (2013.01)

(58) Field of Classification Search
None
See application file for complete search history.

(56) References Cited

FOREIGN PATENT DOCUMENTS

EP 0453604 A1 10/1991

OTHER PUBLICATIONS

Sigma-Aldrich catalog entry "Ion Pair Reagents" (available at http://www.sigmaaldrich.com/analytical-chromatography/analytical-products.html?TablePage=8658636).*
Hawks Chemical catalog, Quaternary Ammonium/Phosphonium Salts (available at http://www.hawks-chem.com/index.php/products/quaternary-ammonium-phosphonium-salts/category).*
Titova et al., Journal of Chromatography (1986) 364, 209-214.*
Abbood et al., Journal of Chromatography A (2009) 1216, 3244-3251.*
Cecchi, Critical Reviews in Analytical Chemistry (2008) 38, 161-213.*
Agilent Zorbax ODS datasheet, available at http://www.agilent.com/cs/library/packageinsert/Public/820628-001d.pdf.*
Montalvo B et al:Determination of pterins in urine by high-performance liquid chromatography on C18 columns conditioned with cetyltrimethylammonium bromide ; Dec. 23, 1988.
Ling Zhou et al:The ionic liquid isopropylammonium formate as a mobile phase modifier to improve protein stability during reversed phase liquid chromatography, Dec. 1, 2013.
Tilly Melin A et al: Reversed-phase ion-pair chromatography with an adsorbing stationary phase and a hydrophobic quaternary ammonium in the mobile phase. Dec. 20, 1979.

* cited by examiner

*Primary Examiner* — Marcela M Cordero Garcia
*Assistant Examiner* — Catherine Mader
(74) *Attorney, Agent, or Firm* — Ling Wu; Stephen Yang; Ling and Yang Intellectual Property (57) ABSTRACT

There are only two ways to increase the amount of sample that can be purified by preparative reversed phase high performance liquid chromatography (Prep-RP-HPLC) in a single run: (1) The traditional approach is to use a bigger column (greater amount of stationary phase); and (2) Use displacement chromatography which uses the stationary phase more effectively. This invention describes a unique Prep-RP-HPLC technique that uses a C-18/C-8 derivatized silica coated with a hydrophobic quaternary ammonium salt or quaternary phosphonium salt to result in 7 to 12 fold increase in sample loading (of the crude mixture of organic compounds including synthetic crude peptides) in contrast to the conventional Prep-RP-HPLC technique. This increase in sample loading capacity and output is due to the additional surrogate stationary phase characteristic of the C-18/C8 bound quaternary salt. The quaternary surfactant is bound to the C-18/C-8 chains and silanols of the stationary phase.

24 Claims, 8 Drawing Sheets

PURIFICATION OF ORGANIC COMPOUNDS USING SURROGATE STATIONARY PHASES ON REVERSED PHASE COLUMNS

FIELD OF THE INVENTION

The invention relates to purification of organic compounds using surrogate stationary phases on reversed phase columns. Specifically, the invention provides a preparative HPLC method for purification of organic compounds employing reagents selected from hydrophobic quaternary ammonium salt or quaternary phosphonium salt as a surrogate stationary phase.

BACKGROUND OF THE INVENTION

Reversed phase high performance liquid chromatography (RP-HPLC) is used ubiquitously in academic institutions, forensic laboratories, fine chemicals, and pharmaceutical industries etc. for the analysis, characterization, separation, purification and/or isolation of small organic molecules, natural products, and biologically active molecules such as polypeptides, proteins, and nucleotides. In the pharmaceutical industry, analytical RP-HPLC is used for the release and characterization of raw materials, intermediates, and active pharmaceutical ingredients (APIs). Preparative reversed phase high performance liquid chromatography (Prep-RP-HPLC) is used for the commercial production of Peptide APIs, and most other complex APIs that are not amenable to crystallization.

Preparative RP-HPLC in the elution mode is limited by the loading capacity of the analyte. In the elution preparative RP-HPLC mode, the typical loading capacity of synthetic peptides is in the range of 1 to 2 mgs per ml of packed column volume (viz., 0.1% to 0.2% with respect to total column volume).

The patent application US20120322976 discloses a preparative HPLC of a GLP-1 analog. The loading was 0.225% with respect to total column volume {(about 45 mgs on to a 20 ml C-18 substituted (Octadecyldimethylsilyl) silica resin (particle size: 15 microns)}.

The patent application US20110313131 discloses a preparative HPLC of (Aib 8, 35) GLP-1(7-36)-NH2 at loadings up to 20 g/L (2% with respect to total column volume).

Recent advances in RP-HPLC have focussed on producing spherical silica and development of new bonding chemistries to furnish stationary supports that have improved stability and selectivity. The earlier supports were irregular silica particles that were derivatized with C-18 or C-8 chains, and they suffered from high back pressure. The high back pressure limited their use with respect to quantity that could be purified in a single run, and to relatively smaller diameter columns.

The commercial manufacture of spherical silica that has been derivatized by C-18, C-8, and other ligands has overcome these challenges and has extended the utility of preparative HPLC vastly. These technological advances in the bonded silica supports and process HPLC instrumentation have made possible commercial production of complex peptides such as Fuzeon®, a 36-amino acid peptide, in ton quantities. Unfortunately, these large scale HPLC instruments and the associated column hardware are very costly and restrict the affordability of the methods.

Further, RP-HPLC in the displacement mode has better loading capacity than RP-HPLC in the elution mode but it is arduous to develop. The displacement chromatography is best suited for ion exchange mode, and has found numerous recent applications.

Displacement chromatography utilizes as mobile phase a displacer solution which has higher affinity for the stationary phase material than do the sample components. The key operational feature which distinguishes displacement chromatography from elution chromatography is the use of a displacer molecule.

The U.S. Pat. No. 6,239,262 discloses low molecular weight displacers for protein purification in hydrophobic interaction and reverse phase chromatographic systems.

In displacement chromatography separations, the sample components are introduced in the form of homogeneous sample solution, so that individual components are each delivered at a constant concentration throughout the sample application step. The driving force for separation is that weak binders are displaced from the limited number of binding sites on the stationary phase material by more strongly binding components of the product mixture. This proceeds in a continuous manner until the product and other stronger binders are fully retarded in the earlier part of the chromatography bed, thus permitting the more weakly binding impurities to stay bound to the stationary phase material further along the chromatography bed. Once all sample molecules are bound to the stationary phase, no further movement of these molecules will be observed. A problem which may occur because of such use of homogeneous sample solutions, however, is that molecules of strongly binding components introduced during an early part of sample application may inadvertently be displaced by weaker binders introduced during a later stage of sample application.

Therefore there is a need for a simple, cost effective and scalable Prep-RP-HPLC process for peptides.

OBJECTS OF THE INVENTION

The primary object of the invention is to provide a novel method of purification of organic compounds including peptides using Preparative Reversed Phase High Performance Liquid Chromatography (Prep-RP-HPLC) technique.

Another object of the invention is to provide a method for purification of organic compounds including peptides which has 7 to 10 times greater sample loading capacity, and output compared to the traditional Prep-RP-HPLC technique.

A further object of the invention is to provide such method using surfactants as surrogate stationary phases (SSPs)/additional stationary phases (ASPs).

SUMMARY OF THE INVENTION

In one aspect, the invention provides a method for purifying a multicomponent sample by reverse phase chromatography comprising:
(a) configuring a chromatographic system having a hydrophobic stationary phase;
(b) saturating the chromatographic stationary phase with quaternary ammonium salt or quaternary phosphonium salt;
(c) optionally washing the column after the step (b) with a buffer; and
(d) applying a multicomponent sample to one end of the chromatographic bed comprising of stationary phase saturated with a hydrophobic quaternary ammonium salt or quaternary phosphonium salt; and
(e) eluting the multicomponent sample in a buffer;

(f) recovering the desired component of the sample.

In another aspect the invention provides a method for purifying a multicomponent sample by reverse phase chromatography comprising:
(a) configuring a chromatographic system having a hydrophobic stationary phase;
(b) saturating the chromatographic stationary phase with quaternary ammonium salt or quaternary phosphonium salt;
(c) optionally washing the column after the step (b) with a buffer;
(d) applying a multicomponent sample to one end of the chromatographic bed comprising of stationary phase saturated with a hydrophobic quaternary ammonium salt or quaternary phosphonium salt; and
(e) eluting the multicomponent sample in a buffer containing quaternary ammonium salt or quaternary phosphonium salt; and
(f) recovering the desired component of the sample.

In yet another aspect, the invention provides a method for purifying a multicomponent sample by reverse phase chromatography comprising:
(a) configuring a chromatographic system having a hydrophobic stationary phase;
(b) saturating the chromatographic stationary phase with quaternary ammonium salt or quaternary phosphonium salt;
(c) optionally washing the column after the step (b) with a buffer;
(d) applying a multicomponent sample to one end of the chromatographic bed comprising of stationary phase saturated with a hydrophobic quaternary ammonium salt or quaternary phosphonium salt; and
(e) eluting the multicomponent sample in a buffer;
(f) recovering the desired component of the sample;
(g) treating the equilibrated chromatographic stationary phase with quaternary ammonium salt or quaternary phosphonium salt with sodium tetrafluoroborate; and
(h) washing the treated chromatographic stationary phase after step (g) with a solvent to recover the chromatographic stationary phase from the quaternary ammonium salt or quaternary phosphonium salt.

Still another aspect of the invention is to provide a preparative HPLC method for purification of organic compounds wherein the method has following advantages (1) increased loading (2) limited use of solvents (3) reduced waste disposal (4) ease of operation, and (5) reduced scale of the equipment utilized to chromatograph, elute, concentrate and recover the desired components.

DETAILED DESCRIPTION OF THE INVENTION

First embodiment of the present invention provides a preparative HPLC method for purification of organic compounds employing quaternary ammonium salt as a surrogate stationary phase, wherein the chromatographic stationary phase is hydrophobic.

The quaternary ammonium salt of the present invention has the structure as mentioned below:

wherein R, $R^1$, $R^2$, $R^3$ is selected independently from the group comprising straight or branched alkyl, cyclic hydrocarbons, aromatic group, alkyl substituted aromatic group, aryl substituted alkyl groups; the anion denoted as B herein in the compound represented by the formula (1) includes bis(trifluoromethylsulfonyl)imide, bis(fluorosulfonyl)imide, dicyanamide, halogens, tetrafluoroborate, hexafluorophosphate, trifluoromethanesulfonate, methanesulfonate, trifluoroacetate, thiocyanate, dimethylphosphate, diethylphosphorodithioate, amino acids, etc. Preferably quaternary ammonium salts are tetra-n-butylammonium bromide, tetra-n-butylammonium hydrogen sulfate, tetra-n-butyl-ammonium hydroxide, tetra-n-octylammonium bromide, methyltrioctylammonium chloride, myristyl trimethyl ammonium bromide, cetyl trimethyl ammonium chloride. Most preferably tetra-n-octylammonium bromide Second embodiment of the present invention provides a preparative HPLC method for purification process of organic compounds employing quaternary phosphonium salt as a surrogate stationary phase in hydrophobic stationary phases, preferably C-18, C-4 and C-8 hydrophobic stationary phase.

The quaternary phosphonium salt of the present invention has the structure as mentioned below, wherein R, $R^1$, $R^2$, $R^3$ is selected independently from the group comprising straight or branched alkyl, cyclic hydrocarbons, aromatic group, alkyl substituted aromatic group, aryl substituted alkyl groups; the anion denoted as B herein in the compound represented by the formula (II) includes bis(trifluoromethylsulfonyl)imide, bis(fluorosulfonyl)imide, dicyanamide, halogens, tetrafluoroborate, hexafluorophosphate, trifluoromethanesulfonate, methanesulfonate, trifluoroacetate, thiocyanate, dimethylphosphate, diethylphosphorodithioate, ethyltriphenylphosphonium bromide, ethyltriphenylphosphoniumiodide, butyltriphenylphosphonium bromide, methyltriphenylphosphonium bromide, triphenylphosphonium bromide, butyltriphenylphosphonium chloride.

According to the process of the invention, the concentration of the organic modifier is held at a sufficiently low concentration to ensure/enforce strong binding of the analytes to the stationary phase (s).

The surrogate stationary phase in the present invention refers to a modified hydrophobic stationary phase that is formed after equilibrating the chromatographic hydrophobic stationary phase with quaternary ammonium salt or quaternary phosphonium salt.

The method of the present invention is distinguished from the prior art displacement chromatography in the following way: the method of the present invention for purifying a peptide by reverse phase chromatography involves the step of applying to the hydrophobic stationary phase a mixture comprising organic compounds to be separated after the addition of the additional (surrogate) stationary phase with or without the organic modifier, whereas the reverse phase displacement chromatography as disclosed in the U.S. Pat. No. 6,239,262, PCT publications WO2013052539 and WO2013052087, for separating organic compounds from a mixture involves the step of applying to the hydrophobic stationary phase a mixture comprising organic compounds to be separated before the addition of the displacer with or without the organic modifier.

In various embodiments, the gradient elution can be accomplished, for example, stepwise, linearly, with multi segmented linear or stepwise changes in composition, or with a combination thereof. In one aspect, gradient elution is performed with increasing amounts of an organic modifier and elution is completed in greater than about 10%, greater than about 20%, greater than about 30%, greater than about 90%, or up to and including about 100% of the organic modifier. In certain aspects, elution is completed with decreasing amount of organic modifier, e.g., less than about 20%, less than about 15%, less than about 10%, less than about 5%, less than about 2%, less than about 1% or about 0% of organic modifier.

The organic modifier in the present invention refers to a solvent or a compound which can be used in chromatographic procedures and like separation methods, to alter the properties of the mobile phase to controllably effect serial elution of desired materials. In one aspect, an organic modifier decreases ionic interactions between molecules in the mobile phase and the stationary phase. For example, in one aspect, an organic modifier comprises a solvent added to a mobile phase to decrease its polarity. Suitable organic modifiers include, but are not limited to, acetonitrile, ethanol, methanol, ethanol, n-propanol or isopropanol. The separating can be accomplished with any suitable solvent or solvent combination.

The nature of the library comprising the multicomponent mixture useful to be separated in the present invention system essentially is unlimited. Thus, mixtures of organic compounds may be used. Digests of biopolymers, either natural or synthetic, are particularly attractive. Such digests may comprise mixtures of peptides, polysaccharides, polynucleotides, various derivatized forms thereof, and variously sized fragments thereof. The biopolymers may be extracted from plant or animal tissues, diseased or healthy, digested if necessary, or used as is. Such libraries are available in abundance, easy to prepare, may be of lower toxicity and more stable than synthetic peptides, and may be varied and screened systematically.

In an embodiment, the concentration of the quaternary ammonium salt or hydrophobic quaternary phosphonium salt in the organic modifier is increased to effect elution of the analytes. The organic modifier may be used with or without the quaternary ammonium salt or the hydrophobic quaternary phosphonium salt.

Third embodiment of the present invention is to provide a process for the removal of the reagents such as hydrophobic quaternary ammonium salt or quaternary phosphonium from the C-18 or C-8 column by employing sodium tetrafluoroborate or potassium hexafluorophosphate with organic modifier.

The fourth embodiment of the present invention is to provide a method for purifying a multicomponent sample by reverse phase chromatography comprising:
(a) configuring a chromatographic system having a hydrophobic stationary phase;
(b) saturating the chromatographic stationary phase with quaternary ammonium salt or quaternary phosphonium salt;
(c) optionally washing the column after the step (b) with a buffer to remove any unbound quaternary salt;
(d) applying a multicomponent sample to one end of the chromatographic bed comprising of stationary phase saturated with a hydrophobic quaternary ammonium salt or quaternary phosphonium salt; and
(e) eluting the multicomponent sample in a buffer; and
(f) recovering the desired component of the sample.

In another aspect, the invention provides a method for purifying a multicomponent sample by reverse phase chromatography comprising:
(a) configuring a chromatographic system having a hydrophobic stationary phase;
(b) saturating the chromatographic stationary phase with quaternary ammonium salt or quaternary phosphonium salt;
(c) optionally washing the column after the step (b) with a buffer to remove any unbound quaternary salt;
(d) applying a multicomponent sample to one end of the chromatographic bed comprising of stationary phase saturated with a hydrophobic quaternary ammonium salt or quaternary phosphonium salt; and
(e) eluting the multicomponent sample in a buffer containing quaternary ammonium salt or quaternary phosphonium salt; and
(f) recovering the desired component of the sample.

In yet another aspect, the invention provides a method for purifying a multicomponent sample by reverse phase chromatography comprising:

(a) configuring a chromatographic system having a hydrophobic stationary phase;
(b) saturating the chromatographic stationary phase with quaternary ammonium salt or quaternary phosphonium salt;
(c) optionally washing the column after the step (b) with a buffer to remove any unbound quaternary salt;
(d) applying a multicomponent sample to one end of the chromatographic bed comprising of stationary phase saturated with a hydrophobic quaternary ammonium salt or quaternary phosphonium salt; and
(e) eluting the multicomponent sample in a buffer;
(f) recovering the desired component of the sample;
(g) treating the chromatography stationary phase saturated/coated with quaternary ammonium salt or quaternary phosphonium salt with sodium tetrafluoroborate; and
(h) washing the treated chromatographic stationary phase after step g with a solvent to recover the chromatographic stationary phase from the quaternary ammonium salt or quaternary phosphonium salt.

Conventional RPLC hardware systems may be used for the separation, and the term "configuring a chromatographic system" refers to setting up a column or system of column, pump and detector as is well known in the art.

The term "saturating the chromatographic stationary phase" refers to passing the quaternary ammonium salt or quaternary phosphonium salt in a solution over the stationary phase in a particular concentration, thereby preparing the surrogate stationary phase.

In a preferred embodiment of the invention, wherein preparative HPLC method for purification of organic compounds maintains a low concentration of the organic modifier to retain the surrogate stationary phase on the column. The said conditions are required for the interaction of surrogate stationary phase with solute along with interaction with C-18, C-4 and C-8 ligands.

Some aspects and embodiments of this disclosure are described in the examples below, which are provided only for the purpose of illustration and are not intended to limit the scope of the disclosure in any manner.

Illustrative Example of the Present Invention

The C-18/C-8 reversed phase column is equilibrated with 5 to 10 column volumes ($V_c$s) of 5 to 10% aqueous acetonitrile containing 10 mM tetra-n-butylammonium hydrogen sulphate (TBAHS, Buffer A). The pH of the starting buffer was not adjusted, and was about 1.95 (It is important to keep the concentration of acetonitrile lower than the concentration needed to elute the product on an analytical HPLC column). The crude compound to be purified was dissolved in starting buffer A or aqueous TFA or aqueous HOAc and loaded on to the column. After the loading is complete, the column is equilibrated with 2 Column $V_c$s of Buffer A. Next, the gradient elution process is started. The buffer B is usually 300 mM to 500 mM TBAHS in 5 to 10% aqueous acetonitrile. A linear gradient of 0% B to 100% Buffer B over 10 $V_c$s is applied. When the product of interest (API) is about to elute, a gradient hold may be applied until all the API has eluted from the column. Alternately if it is desired to elute the product in a concentrated form the gradient may be allowed to run its course. The fractions containing the pure API product are combined after confirming that the pooled fraction meets the purification criteria. The approximate quantity of the associated TBAHS is calculated. This is then treated with 1.5 to 2 equivalents of sodium tetrafluoroborate ($NaBF_4$) and extracted 3 times with chloroform to remove the TBA cation as its tetrafluoroborate salt. The aqueous residue is then loaded on to a C-18/C-8 column from which all the TBAHS (quaternary ammonium/phosphonium salt) has been removed. Removal of TBAHS from the C-18/C-8 column is accomplished by the following steps: The column is first washed with at least 3 $V_c$s of 80% Acetonitrile-20% Water. Next, the column is washed with 3$V_c$s of 100 mM $NaBF_4$ in 80% Acetonitrile-20% water. The column is equilibrated with 1M Acetic Acid in 1% Aqueous Acetonitrile (10 $V_c$s). The aqueous phase containing "pure API" and excess $NaBF_4$ is diluted with water (5× its volume) and loaded on to the C-18/C-8 column on to the column. The column is washed with 5 to 10 $V_c$s of 1% phosphoric acid-1% Acetonitrile-98% Water to exchange the $BF_4$ anions for phosphate anions. The column is then washed with 5 to 10 $V_c$s of 100 mM aqueous Guanidine. HCl to remove the phosphate anions and to exchange the phosphate anions to chloride anions. Finally the chloride anions are exchanged for acetate anions. The fractions containing the "pure product acetate salt" are combined, and the organic volatiles are removed under reduced pressure. The aqueous residue is lyophilized or precipitated after removal of water. The final API is analysed according to the USP/EP Methods of Analysis.

TABLE 1

Purification of Leuprolide: Comparison of the Surrogate Stationary Phase aided Prep-RP-HPLC with the Standard Prep-RP-HPLC

| Entry # | Prep RP-HPLC method | Column dimensions; (ID × L) | Total Column volume (mL) | Input: Crude API (g) | Output: Pure API (g) | % Yield | % Purity by HPLC (USP method) | Relative Loading Capacity |
|---|---|---|---|---|---|---|---|---|
| 1. | Standard RP-HPLC [Comparative example] | YMC, ODS-AQ (50 mm × 250 mm, C18, 10 u, 120 Å pore diameter) | 490.0 | 4.0 g | 1.2 g | 30.0% | 99.86 | 1 |
| 2. | SSP-Purification method [TBAHS-SSP] | Waters Symmetry (19 mm × 50 mm, C8, 5 u, 120 Å pore diameter) | 14.2 | 1.4 g | 0.42 g | 30.0% | 99.79 | 12.1 |
| 3. | SSP-Purification method [TBAHS-SSP] | Discovery Bio Wide Pore (10 mm × 250 mm, C18, 5 u, 300 Å pore diameter) | 19.6 | 1.2 g | 0.32 g | 26.7% | 99.73 | 6.7 |

The purified product (Leuprolide) output of the standard Prep-RP-HPLC is 2.45 mg/mL of column volume: In contrast the purified product output of the surrogate stationary phase aided Prep-RP-HPLC is 29.6 mg/mL of column volume (table 1, entry 2) and 16.3 mg/mL of column volume (table 1, entry 3). These results suggest that loadings of 7 to 12 times capacity of conventional prep-RP-HPLC are achievable with the processes described in the present invention.

EXAMPLES

Example-1: Preparative RP-HPLC of Leuprolide Acetate

Figure 1:
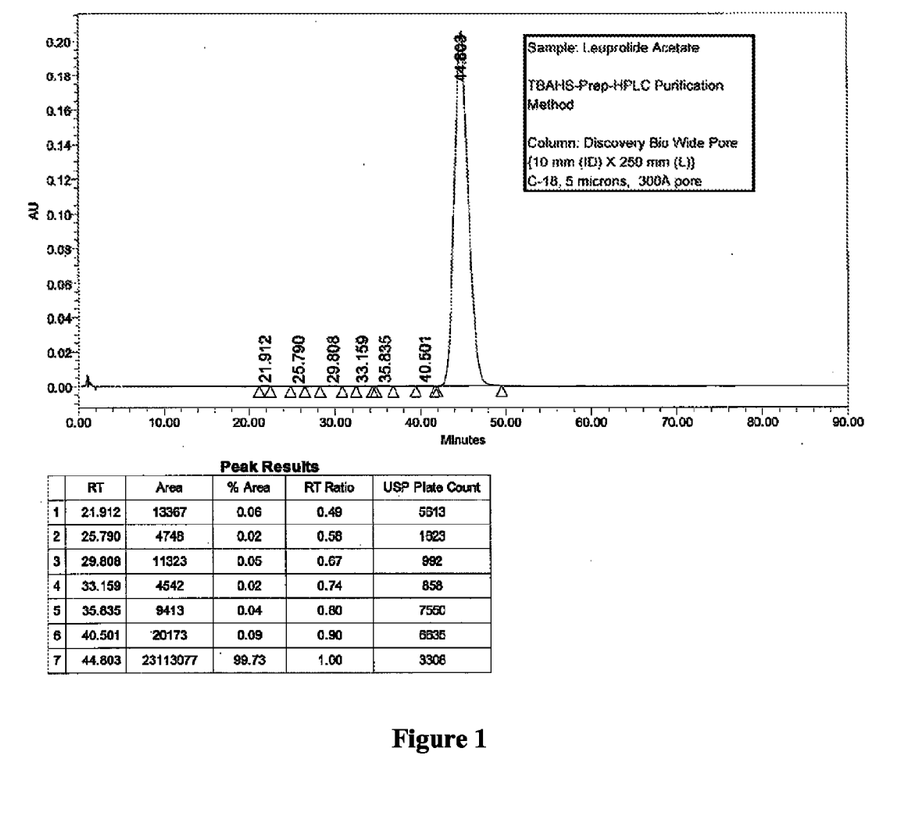
FIG. 1: Analytical RP-HPLC profile of Leuprolide acetate obtained using the present invention. A Discovery Bio Wide Pore (10 mm×250 mm, C18, 5 u, and 300Å pore diameter) column was used for the Prep-RP-HPLC process.
Figure 2:
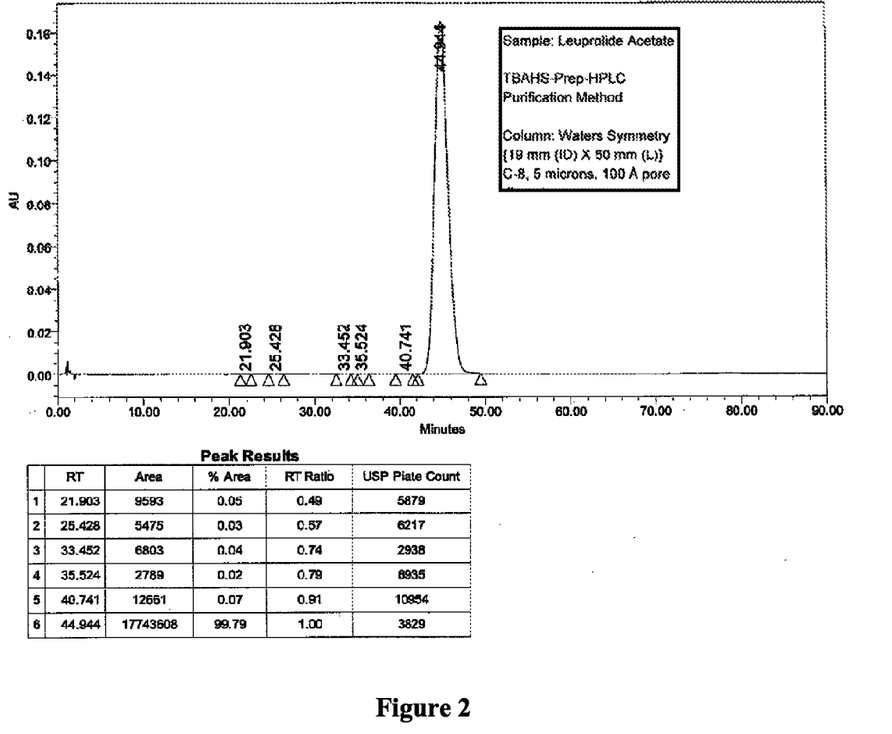
FIG. 2: Analytical RP-HPLC profile of Leuprolide acetate obtained using the present invention. A Waters Symmetry (19 mm×50 mm, C8, 5 u, 120 Åpore diameter) column was used for the Prep-RP-HPLC process.
Figure 3:
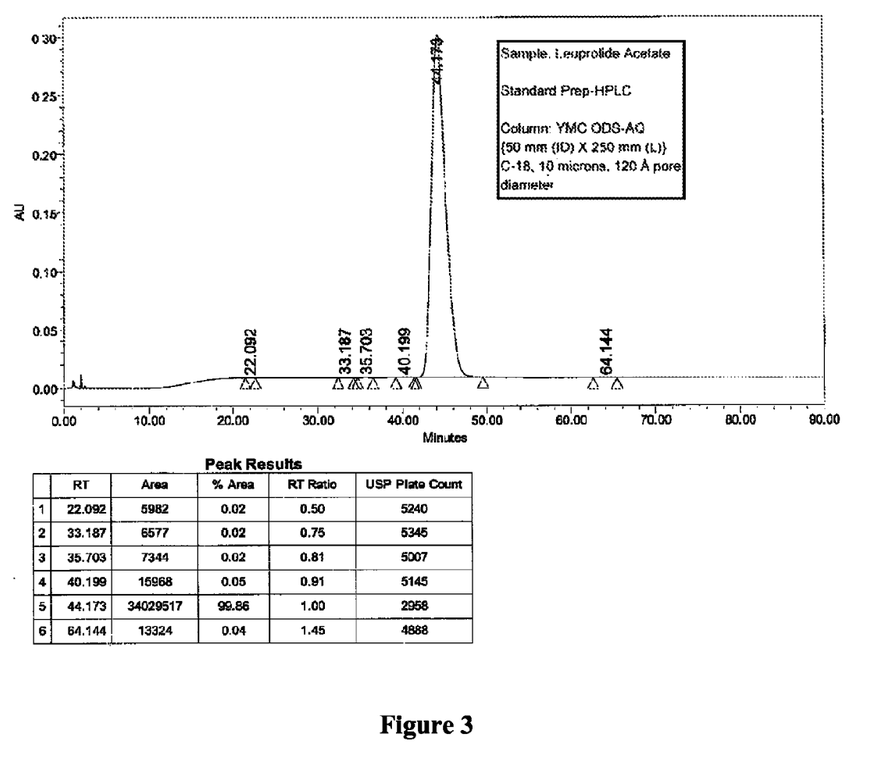
FIG. 3: Analytical RP-HPLC profile of Leuprolide acetate by obtained using standard (conventional) preparative RP-HPLC technique. A YMC, ODS-AQ (50 mm×250 mM, C18, 10μ, 120° A pore diameter [see comparative example] was used for the Prep-RP-HPLC process.

Two different columns were evaluated for the purification of Leuprolide: A Discovery Bio Wide Pore column {column parameters: 10 mm (ID)×250 mm (L), C18, 5 u particles, 300Å pore diameter, Amount loaded was 1.2 g of crude Leuprolide (prepared by solution phase synthesis) and a Waters Symmetry Column {column parameters: 19 mm (Internal Diameter, ID)×50 mm (Length, L), C8, 5 u particles, 120 Åpore diameter, Amount loaded was 1.4 g of crude Leuprolide (prepared by solution phase synthesis) were used. The column was pre-equilibrated with 5 to 10 column volumes ($V_c$s) of 10 mM TBAHS in 10% aqueous acetonitrile (Buffer A). After the loading was complete, the column was washed with 2 $V_c$s of Buffer A. Next, the gradient elution process was started. The buffer B was 300 mM TBAHS in 10% aqueous acetonitrile. A linear gradient of 0% B to 100% Buffer B over 60 min. was used for elution. A gradient hold was applied until all the API has eluted from the column. The fractions containing the pure API product were combined and treated with 1.5 to 2 equivalents of sodium tetrafluoroborate (NaBF$_4$) and extracted 3 times with chloroform. The entire purification process was repeated 3 times to demonstrate and confirm the consistent performance. Fractions containing "pure Leuprolide" were combined and loaded on to a C-18 column from which all the TBAHS had been removed as described before.

The conversion of phosphate/hydrogen sulphate anions to acetate anions was done as described earlier. Fractions containing pure Leuprolide Acetate API were lyophilized. The purification yield was about 30%. (TBA-HS herein denotes tetra-n-butyl-ammonium hydrogen sulphate)

Example-2: Preparative RP-HPLC of Triptorelin Acetate

The C-18/C-8 reversed phase column was pre-equilibrated with 5 to 10 $V_c$s of 5 to 10% aqueous acetonitrile containing 10 mM TBAHS (Buffer A). A Discovery Bio Wide Pore column {column parameters: 10 mm (ID)×250 mm (L), C18, 5 u particles, 300Å pore diameter, Amount loaded was 1.0 g of crude Triptorelin} was used. After the loading was complete, the column was washed with 2 $V_c$s of Buffer A. Next, the gradient elution process was started. The buffer B was 300 mM TBAHS in 10% aqueous acetonitrile. A linear gradient of 0% B to 100% Buffer B over 60 min. was used for elution. A gradient hold was applied until all the API has eluted from the column. The fractions containing the pure API product were combined and treated with 1.5 to 2 equivalents of sodium tetrafluoroborate (NaBF$_4$) and extracted 3 times with chloroform. The entire purification process was repeated 3 times to demonstrate and confirm the consistent performance. Fractions containing "pure Triptorelin" were combined and loaded on to a C-18 column from which all the TBA-HS had been removed as described before.

The conversion of phosphate/hydrogen sulphate anions to acetate anions was done as described earlier. Fractions containing pure Triptorelin API were lyophilized. The purification yield was about 25%. (TBAHS herein denotes tetra-n-butyl-ammonium hydrogen sulphate)

Example-3: Preparative RP-HPLC of Leuprolide Acetate Employing Tetra-n-Butylammonium Bromide (TBA-Br)

Figure 4:
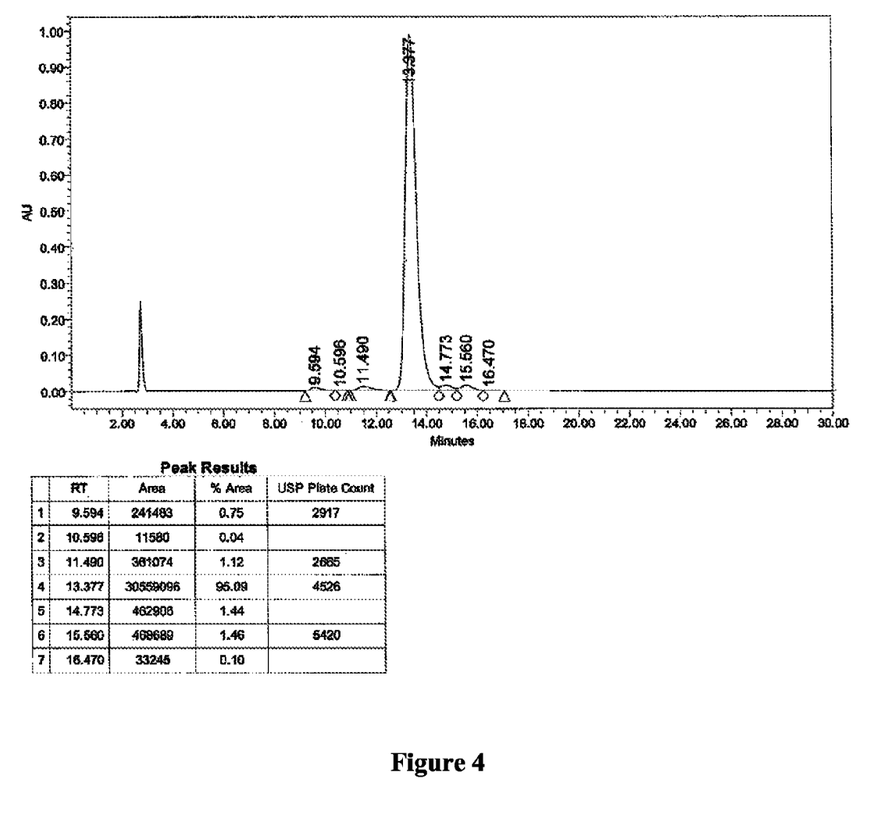
FIG. 4: Analytical RP-HPLC profile of Leuprolide acetate (pooled preparative HPLC fractions that were greater than 95% pure) obtained using tetra-n-butylammonium bromide (TBA-Br) and a Grace Vydac C18 column (40 micron particles).

The C-18 reverse phased column [Grace Vydac Column parameters 12 g of C-18, 40 microns particles, 60 Å pore diameter] was saturated with 36 g of TBA-Br in 360 mL of water at the flow rate of 8.0 ml/min. The column was then equilibrated 10 $V_c$s with Buffer A (25 mM TBA-Br in water) at a flow rate of 8.0 ml/min. The crude leuprolide trifluoroacetate salt was dissolved in Buffer A and loaded on to the column. After the loading is complete, the gradient elution process was started. The Buffer B is 25 mM of TBA-Br in 50% aqueous acetonitrile. A linear gradient of 0% of Buffer B to 100% of Buffer B over 10 $V_c$s was applied. When Leuprolide is about to elute, a gradient hold may be applied until all the API has eluted from the column. The fraction containing the pure Leuprolide is combined after confirming the purity on an analytical HPLC. Yield: 66.4%. Herein TBA-Br is tetra-n-butylammonium bromide.

Removal of TBA-Br from the C-18 column: The column was first washed with at least 5 $V_c$s of 0.1 M sodium tetrafluoroborate in acetonitrile and water (8:2) followed by aqueous acetonitrile.

Example-4: Preparative RP-HPLC of Leuprolide Acetate Employing Tetra-n-Butylammonium Hydrogen Sulfate (TBA-HS)

Figure 5:
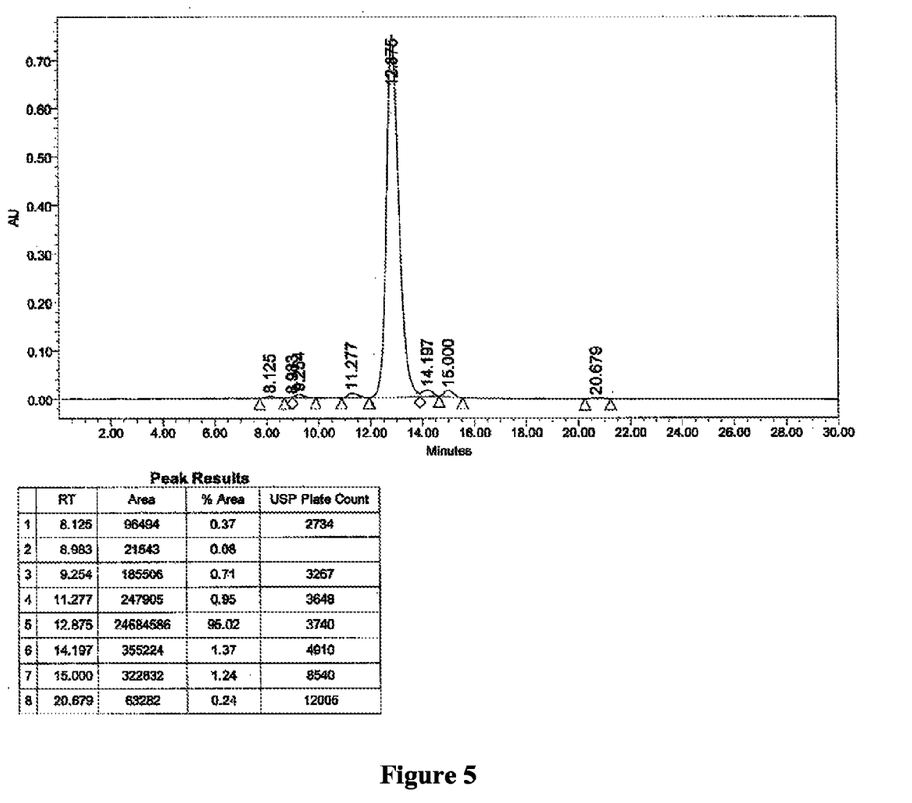
FIG. 5: Analytical RP-HPLC profile of Leuprolide acetate (pooled preparative HPLC fractions that were greater than 95% pure) obtained using tetra-n-butylammonium hydrogen sulfate (TBA-HS) and a Grace Vydac C18 column (40 micron particles).

The C-18 reverse phased column [Grace Vydac Column parameters 12 g of C-18, 40 microns particles, 60 Å pore diameter] was saturated with a solution of 36 g of TBA-HS in 360 mL of water at a flow rate of 8.0 ml/min. The column was then equilibrated with Buffer A (25 mM TBA-HS in water) about 10 $V_c$s at a flow rate of 8.0 ml/min. The crude leuprolide trifluoroacetate salt was dissolved in Buffer A and loaded on to the column. After the loading is complete, the gradient elution process was started. The Buffer B is 25 mM of TBA-HS in 50% aqueous acetonitrile. A linear gradient of 0% of Buffer B to 100% of Buffer B over 10 $V_c$s was applied. When Leuprolide is about to elute, a gradient hold may be applied until all the API has eluted from the column. The fractions containing the pure Leuprolide are combined after confirming the purity on an analytical HPLC. Yield: 64.4%. Herein TBAHS is tetra-n-butylammonium hydrogen sulfate.

Removal of TBA-HS from the C-18 column: The column was first washed with at least 5 column volumes of 0.1M sodium tetrafluoroborate in acetonitrile and water (8:2) followed by aqueous acetonitrile.

Example-5: Preparative RP-HPLC of Leuprolide Acetate Employing Cetyltrimethylammonium Bromide (CTA-Br)

Figure 6:
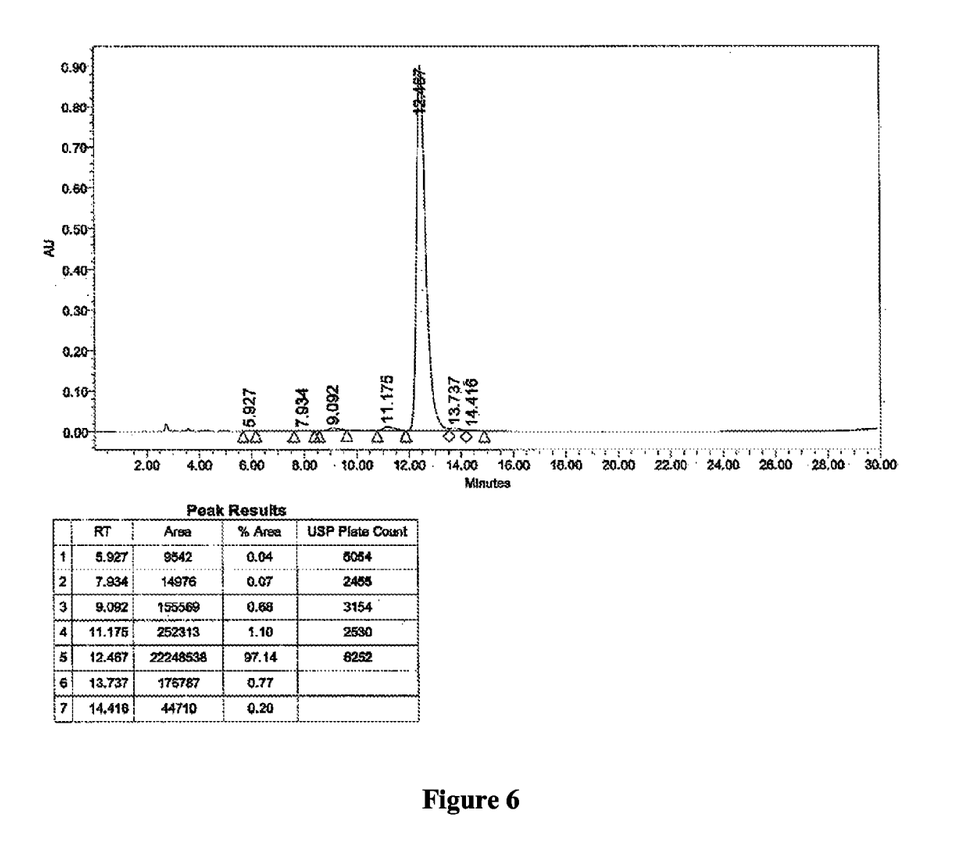
FIG. 6: Analytical RP-HPLC profile of Leuprolide acetate (pooled preparative HPLC fractions that were greater than 95% pure) obtained using cetyltrimethylammonium bromide (CTA-Br) and a Grace Vydac C-18 column (40 micron particles).

The C-18 reverse phased column [Grace Vydac Column parameters 12 g of C-18, 40 microns particles, 60 Å pore diameter] was saturated with solution of 1 mM CTA-Br in water at a flow rate of 8.0 ml/min. The column was then equilibrated with Buffer A (5 mM CTA-Br in water) about 10 $V_c$s at a flow rate of 8.0 ml/min. The crude leuprolide trifluoroacetate salt was dissolved in Buffer A and loaded on to the column. After the loading is complete, the gradient elution process was started. The Buffer B is 5 mM of CTA-Br in 50% aqueous acetonitrile. A linear gradient of 0% of Buffer B to 100% of Buffer B over 10 $V_c$s was applied. When Leuprolide is about to elute, a gradient hold may be applied until all the API has eluted from the column. The fractions containing the pure Leuprolide are combined after confirming the purity on an analytical HPLC. Yield: 61.4%. Herein CTA-Br is cetyltrimethylammonium bromide.

Removal of CTA-Br from the C-18 column: The column was first washed with at least 5 $V_c$s of 0.1M sodium tetrafluoroborate in acetonitrile and water (8:2) followed by aqueous acetonitrile.

Example-6: Preparative RP-HPLC of Leuprolide Acetate Employing Tetra-n-Butylphosphonium Chloride (TBP-Cl)

Figure 7:
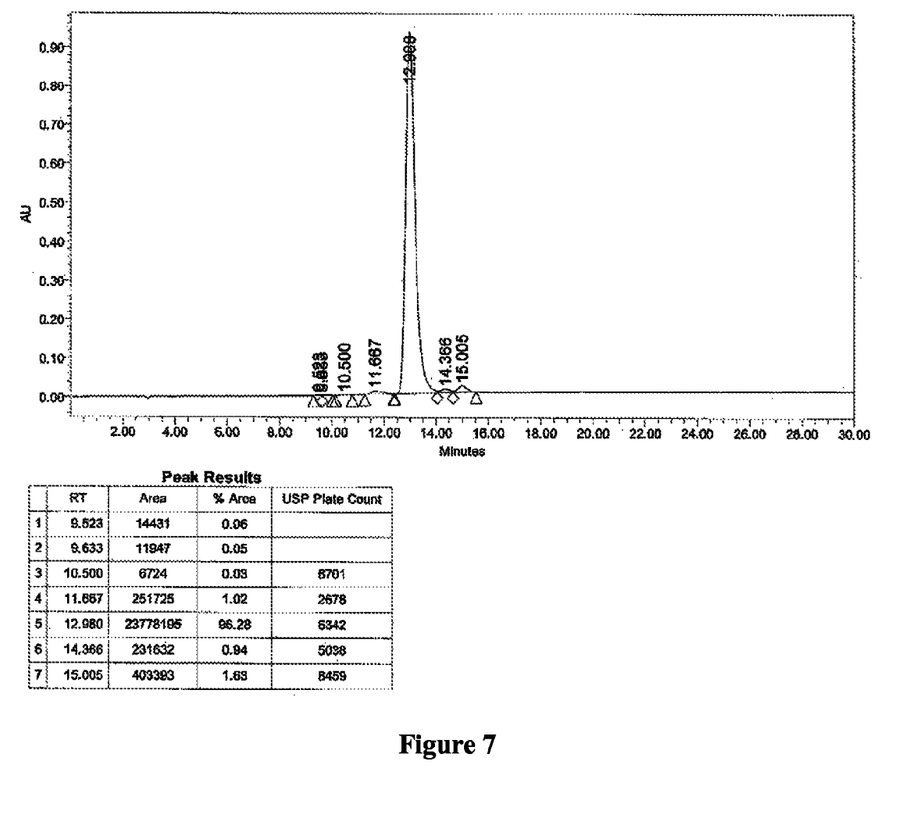
FIG. 7: Analytical RP-HPLC profile of Leuprolide acetate (pooled preparative HPLC fractions that were greater than 95% pure) obtained using tetra-n-butylphosphonium chloride (TBP-Cl) and a Grace Vydac C-18 column (40 micron particles).

The C-18 reverse phased column [Grace Vydac Column parameters 12 g of C-18, 40 microns particles, 60 Å pore diameter] was saturated with solution of 36 g of TBP-Cl in 360 ml of water at a flow rate of 8.0 ml/min. The column was then equilibrated with Buffer A (25 mM TBP-Cl in water) about 10 $V_c$s at a flow rate of 8.0 ml/min. The crude leuprolide trifluoroacetate salt was dissolved in Buffer A and loaded on to the column. After the loading is complete, the gradient elution process was started. The Buffer B is 25 mM of TBP-Cl in 50% aqueous acetonitrile. A linear gradient of 0% of Buffer B to 100% of Buffer B over 10 Column volumes was applied. When Leuprolide is about to elute, a gradient hold may be applied until all the API has eluted from the column. The fractions containing the pure Leuprolide are combined after confirming the purity on an analytical HPLC. Yield: 60.3%. Herein TBP-Cl is tetra-n-butylphosphonium chloride.

Removal of TBP-Cl from the C-18 column: The column was first washed with at least 5 $V_c$s of 0.1M sodium tetrafluoroborate in acetonitrile and water (8:2) followed by aqueous acetonitrile.

Example-7: Preparative RP-HPLC of Leuprolide Acetate Employing Tetra-n-Butylammonium Chloride (TBA-Cl)

Figure 8:
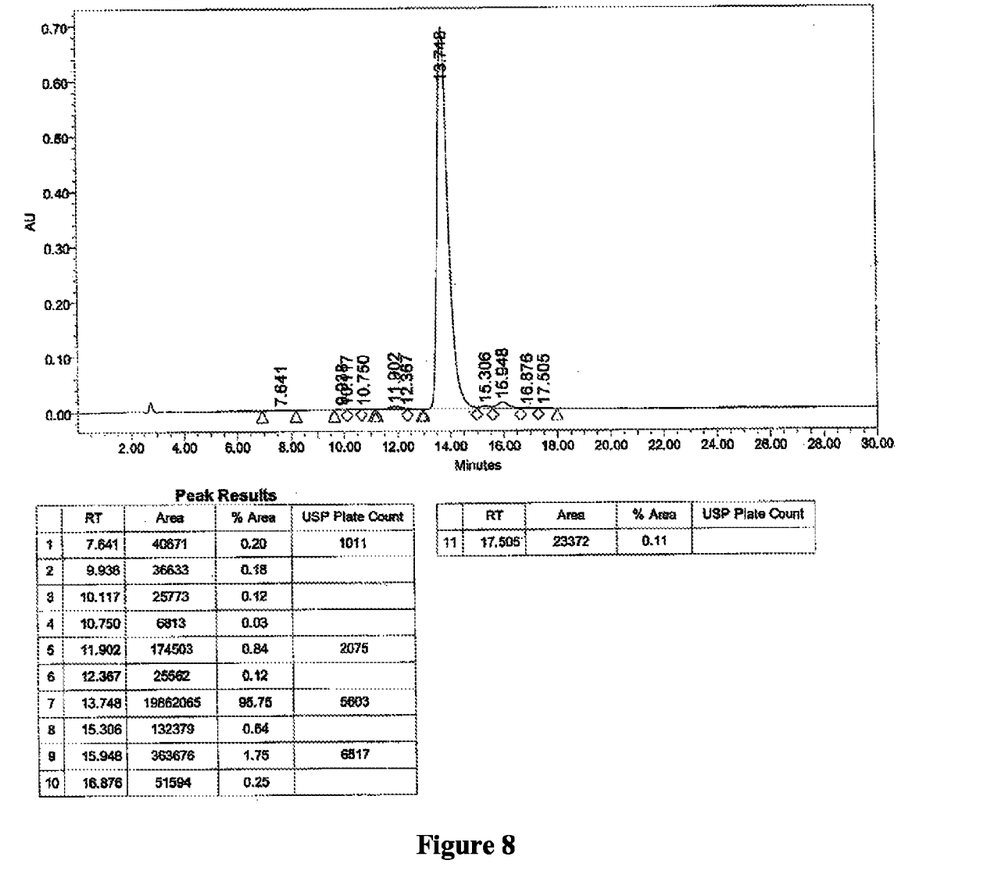
FIG. 8: Analytical RP-HPLC profile of Leuprolide acetate (pooled preparative HPLC fractions that were greater than 95% pure) obtained using tetra-n-butylammonium chloride (TBA-Cl) and a Grace Vydac C-18 column (40 micron particles).

The C-18 reverse phased column [Grace Vydac Column parameters 12 g of C-18, 40 microns particles, 60 Å pore diameter] was saturated with 36 gm of TBA-Cl in 360 ml of water at a flow rate of 8.0 ml/min. The column was then equilibrated with Buffer A (25 mM TBA-Cl in water) about 10 $V_c$s at a flow rate of 8.0 ml/min. The crude leuprolide trifluoroacetate salt was dissolved in Buffer A and loaded on to the column. After the loading is complete, the gradient elution process was started. The Buffer B is 25 mM of TBA-Cl in 50% aqueous acetonitrile. A linear gradient of 0% of Buffer B to 100% of Buffer B over 10 $V_c$s was applied. When Leuprolide is about to elute, a gradient hold may be applied until all the API has eluted from the column. The fractions containing the pure Leuprolide are combined after confirming the purity on an analytical HPLC. Yield: 53.5%. Herein TBA-Cl is tetra-n-butylammonium chloride.

Removal of TBA-Cl from the C-18 column: The column was first washed with at least 5 $V_c$s of 0.1M sodium tetrafluoroborate in acetonitrile and water (8:2) followed by aqueous acetonitrile.

What is claimed is:

1. A method of purification of organic compounds using a C-18/C-8 preparative reversed phase column that has a physically adsorbed surrogate stationary phase which increases the sample loading capacity by 7 to 12 fold.

2. The method as claimed in claim 1, wherein the preparative loading capacity of C-18/C-8 reversed phase column is increased by physical adsorption of a hydrophobic quaternary ammonium salt or hydrophobic quaternary phosphonium salt as a surrogate stationary phase.

3. The method as claimed in claim 2, which comprises:
   a) saturating a preparative C-18/C-8 column with a cationic surfactant surrogate stationary phase selected from tetraalkylammonium salts or tetralkylphosphonium salts;
   (b) washing the column to remove excess unbound surfactant employing a mixture of organic solvents and water;
   (c) equilibrating the column with the starting mobile phase;
   (d) applying a multicomponent sample to one end of the chromatographic bed comprising stationary phase coated with the quaternary ammonium surfactants;
   (e) eluting the multicomponent sample using a linear gradient of buffers A & B, wherein the buffer A is water containing tetraalkylammonium salt (0 mM to 500 mM) and buffer B is 5 to 10% aqueous acetonitrile containing 300 mM to 500 mM tetraalkylammonium salt; or
   (f) eluting the multicomponent sample using a linear gradient of buffers A & B, wherein the buffer A is 5 to 10% aqueous acetonitrile containing tetraalkylammonium salt (0 mM to 500 mM) and buffer B is 300 mM to 500 mM tetraalkylammonium salt in 10 to 80% aqueous acetonitrile; or
   (g) eluting the multicomponent sample using a linear gradient of buffers A & B, wherein the buffer A is water containing 0 mM to 25 mM tetraalkylammonium salt, and buffer B is 0 mM to 25 mM tetraalkylammonium salt in 50 to 80% aqueous acetonitrile; or
   (h) eluting the multicomponent sample using a linear gradient of buffers A & B, wherein the buffer A is 1 mM to 5 mM cetyltrimethylammonium bromide (CTA-Br) and buffer B is 5 mM CTA-Br in 50% aqueous acetonitrile; or
   (i) eluting the multicomponent sample using a linear gradient of buffers A & B, wherein the buffer A is water containing 0 mM to 25 mM tetraalkylphosphonium salt, and buffer B is 0 mM to 25 mM tetraalkylphosphonium salt in 50 to 80% aqueous acetonitrile;
   (j) and recovering the desired component of the sample.

4. The method as claimed in claim 3 comprises removing quaternary ammonium surrogate stationary phase coating from the C-18/C-8 derivatized silica by washing the column in succession with sodium tetrafluoroborate or potassium hexafluorophosphonate.

5. The method as claimed in claim 3, wherein the residual quaternary ammonium salt from the desired purified product is extracted into organic solvent after converting the anion to tetrafluoroborate or hexafluorophosphonate.

6. The method as claimed in claim 3, wherein the quaternary ammonium salt is tetrabutylammonium hydrogen sulphate or tetraoctylammonium bromide.

7. The method as claimed in claim 5, wherein the organic solvent is a water immiscible solvent.

8. The method as claimed in claim 5, wherein the water immiscible solvent is chloroform or ethyl acetate.

9. The method as claimed in claim 3, wherein the surfactants in step (a) are selected from the group consisting of tetra-n-butylammonium bromide, tetra-n-butylammonium chloride, tetra-n-butylammonium hydrogen sulfate, tetra-n-butylammonium hydroxide, tetra-n-octylammonium bromide, methyltrioctylammonium chloride, myristyltrimethylammonium bromide or cetyltrimethylammonium chloride.

10. The method as claimed in claim 3, wherein the washing of the column in step (c) with aqueous acetonitrile contains 0.1% trifluoroacetic acid to remove the unbound surfactant.

11. The method as claimed in claim 4, wherein the aqueous acetonitrile is 90% aqueous acetonitrile.

12. The method as claimed in claim 3, wherein equilibration comprises equilibrating the column with mobile phase.

13. The method as claimed in claim 3, wherein the organic solvent is water immiscible solvent.

14. The method as claimed in claim 13, wherein water immiscible solvent is chloroform or ethyl acetate.

15. The method as claimed in claim 2, wherein the surrogate stationary phase is a hydrophobic quaternary ammonium salt, and the general structure is shown below:

wherein R, $R^1$, $R^2$ & $R^3$ are selected independently from the group comprising straight or branched alkyl, cyclic hydrocarbons, aromatic group, alkyl substituted aromatic group, aryl substituted alkyl groups; heteroaromatic groups, and $B^-$ denotes an anion.

16. The method as claimed in claim 15, wherein the anion is selected from the group consisting of halogen, acetate, hydrogen sulphate, sulphate, tetrafluoroborate, hexafluorophosphate, trifluoromethanesulfonate, methanesulfonate, trifluoroacetate, thiocyanate, amino acids, oxalate, maleate, succinate, citrate or tartrate.

17. The method as claimed in claim 3, wherein the hydrophobic stationary phase in step (a) is C-8 or C-18 alkyl chain derivatized silica.

18. The method as claimed in claim 2, wherein the said surrogate stationary phase is a hydrophobic quaternary phosphonium salt, and the general structure is shown below:

wherein R, $R^1$, $R^2$, $R^3$ are selected independently from the group comprising straight or branched alkyl, cyclic hydrocarbons, aromatic group, alkyl substituted aromatic group, aryl substituted alkyl groups; heteroaromatic groups, and B denotes an anion.

19. The method as claimed in claim 18, wherein the anion is selected from the group consisting of halogen, acetate, hydrogen sulphate, sulphate, tetrafluoroborate, hexafluorophosphate, trifluoromethanesulfonate, methane sulfonate, trifluoroacetate, thiocyanate, amino acids, oxalate, maleate, succinate, citrate or tartrate.

20. The method as claimed in claim 18, wherein the quaternary phosphonium salt is tetra-n-butylphosphonium chloride.

21. The method as claimed in claim 3, which comprises removing the quaternary phosphonium surrogate stationary phase coating from the C-18/C-8 derivatized silica by washing the column in succession with sodium tetrafluoroborate or potassium hexafluorophosphonate.

22. The method as claimed in claim 3, wherein the residual quaternary phosphonium salt from the desired purified product is extracted into organic solvent after converting the anion to tetrafluoroborate or hexafluorophosphonate.

23. The method as claimed in claim 22, wherein the organic solvent is ethyl acetate or chloroform.

24. The method as claimed in claim 1, wherein the organic compounds include peptides.

* * * * *